US006883722B2

(12) United States Patent
Pankow

(10) Patent No.: US 6,883,722 B2
(45) Date of Patent: Apr. 26, 2005

(54) PORTABLE RELAXATION AND THERAPY DEVICE AND KIT

(75) Inventor: Greg Pankow, Morton Grove, IL (US)

(73) Assignee: Walgreen Co., Deerfield, IL (US)

( * ) Notice: Subject to any disclaimer, the term of this patent is extended or adjusted under 35 U.S.C. 154(b) by 331 days.

(21) Appl. No.: 10/102,417

(22) Filed: Mar. 20, 2002

(65) Prior Publication Data

US 2003/0178502 A1 Sep. 25, 2003

(51) Int. Cl.$^7$ .............................................. B05B 17/08
(52) U.S. Cl. .......................... 239/17; 239/23; 239/193; 239/211; 239/289; 40/406
(58) Field of Search ............................. 239/17, 22, 23, 239/193, 211, 289, 20; 40/406; D23/201

(56) References Cited

U.S. PATENT DOCUMENTS

| | | | | |
|---|---|---|---|---|
| 5,167,368 A | * | 12/1992 | Nash | 239/17 |
| 5,934,557 A | * | 8/1999 | Shih | 239/17 |
| 6,029,899 A | * | 2/2000 | Walker | 239/17 |
| 6,206,298 B1 | * | 3/2001 | Ting | 239/20 |
| 6,382,520 B1 | * | 5/2002 | Hones | 239/193 |
| 6,439,471 B2 | * | 8/2002 | Ehrlich et al. | 239/289 |
| 6,447,137 B1 | * | 9/2002 | Long | 239/17 |
| 6,527,257 B1 | * | 3/2003 | Schuld | 239/23 |

OTHER PUBLICATIONS

*Candle Therapy. Other Worldly Waxes*, (visited Feb. 20, 2002) <http://www.candletherapy.com/ >.
*Feng Shui and Water Fountains*, (visited Feb. 20, 2002) <http://www.aquaarts.com/feng_shui/feng_shui.html>.
*Candles*, (visited Feb. 20, 2002) <http://www.candletherapy.com/page33.htm>.
*Aromatherapy Candles from Pure Essential Oils*, (visited Feb. 20, 2002) <http://www.aromatherapyoutlet.com/container_candles.htm>.
*A World of Aromatherapy —The History*, (visited Feb. 20, 2002) <http://www.aworldofaromathereapy.com/aromatherapy–origins.htm>.
*Aromatherapy Today*, (visited Feb. 20, 2002) <http://www.aworldofaromatherapy.com/aromatherapy–today.htm>.

* cited by examiner

Primary Examiner—Steven J. Ganey
(74) Attorney, Agent, or Firm—Marshall, Gerstein & Borun LLP

(57) ABSTRACT

A portable relaxation and therapy device or kit includes a liquid retention basin having a bottom wall and a perimeter wall upstanding from the bottom wall to define at least one liquid chamber therewithin. A waterfall is provided having a reflecting surface extending generally upwardly from the retention basin to a liquid dispersing waterfall ledge thereabove. The device or kit includes a pump disposed in the liquid chamber in communication with a tube for directing liquid in the retention basin upwardly to the waterfall ledge. The waterfall ledge causes liquid to cascade downwardly to the liquid chamber of the retention basin in front of the reflecting surface of the waterfall wall. The device also includes a cover for the retention basin disposed over the liquid chamber so as to overlie and substantially isolate from view liquid in at least a portion of the retention basin. With this arrangement, the cover permits liquid cascading downwardly from the waterfall ledge in front of the reflecting surface of the waterfall wall to return to the liquid chamber.

25 Claims, 4 Drawing Sheets

US 6,883,722 B2

PORTABLE RELAXATION AND THERAPY DEVICE AND KIT

FIELD OF THE INVENTION

The present invention is generally directed to therapy devices and kits and, more particularly, portable relaxation and therapy devices and kits that combine various different types of therapeutics.

BACKGROUND OF THE INVENTION

In recent years, there has been a growing recognition of the role of a number of different types of therapeutics in enhancing the health and well being of the mind, body and spirit. It is generally known, for instance, that many ancient therapies that were developed from things that were naturally available have been rediscovered and placed into common use to thereby take advantage of some of the oldest and most basic forms of holistic healing. Specifically, there is now widespread recognition of the benefits that can be derived from the utilization of candle therapy, waterflow therapy, and aromatherapy among others.

Although these forms of therapeutics have been practiced for thousands of years, it has only been in recent years they have experienced popularity throughout the mainstream of our modem culture. This has come about in no small part as a result of more and more people returning to a holistic lifestyle, recognizing the importance of treating the mind, body and spirit to achieve optimum health and wellness. In this regard, modem day scientific research has verified not only the emotional benefits, but also the physical benefits to be derived from candle therapy, waterflow therapy, and aromatherapy.

In other words, we have once again developed a keen awareness and appreciation of what nature has always offered for achieving health and wellness of the mind, body and spirit. This has come about in response to an ever increasing awareness of the illnesses that pervade society and the stresses that are caused by the fast pace of modem life. While conventional medicine provides some solutions, there is a recognition that nature can provide a complement to conventional medicine to make it possible to live more balanced lives.

From this recognition, there have been significant developments in candle therapy, waterflow therapy, and aromatherapy products and techniques. It seems, however, that each of these therapeutics has developed independently, which means that products for practicing each of these forms of therapy must be purchased and used separately. For this reason, there has been a need for developing a device and kit that combines the benefits of candle therapy, waterflow therapy, and aromatherapy.

SUMMARY OF THE DISCLOSURE

In accordance with one aspect of the disclosure, a portable relaxation and therapy device is provided that includes a liquid retention basin having a bottom wall and a perimeter wall upstanding from the bottom wall to define at least one liquid chamber therewithin. A waterfall wall having a reflecting surface extends generally upwardly from the retention basin to a liquid dispersing waterfall ledge thereabove. The device also includes a pump disposed in the liquid chamber in communication with a tube for directing liquid in the retention basin upwardly to the waterfall ledge thereby causing liquid to cascade downwardly to the liquid chamber of the retention basin in front of the reflecting surface of the waterfall wall. A cover for the retention basin is disposed over the liquid chamber to overlie and substantially isolate from view liquid in at least a portion of the retention basin. With this arrangement, the cover is formed to permit liquid which is cascading downwardly from the waterfall ledge in front of the reflecting surface of the waterfall wall to return to the liquid chamber for recirculation to the waterfall ledge by the pump.

In accordance with another aspect of the disclosure, a plurality of polished stones or rocks and at least one aroma tea candle are preferably placed at a lower end of the reflecting surface of the waterfall wall. The reflecting surface is advantageously disposed at an inwardly and downwardly inclined angle to the vertical when supported by the retention basin to extend generally upwardly. Preferably, the waterfall wall terminates in a pair of splash plates at the lower end thereof at the bottom of the reflecting surface to lead in step-like fashion to the cover when supported by the retention basin.

In accordance with another aspect of the disclosure, the portable relaxation and therapy device can be provided as a kit. The waterfall wall can then be a separate from, but adapted for support by the retention basin, the pump can be removably disposed in the liquid chamber for connection to a tube in the waterfall wall, and the cover can be removably disposed over the liquid chamber. In kit form, the various components can easily be assembled by the purchaser of the portable relaxation and therapy kit.

Other advantages and features of the disclosure will become apparent from a consideration of the following description taken in conjunction with the accompanying drawings.

DETAILED DESCRIPTION OF THE PREFERRED EMBODIMENT

Figure 1:
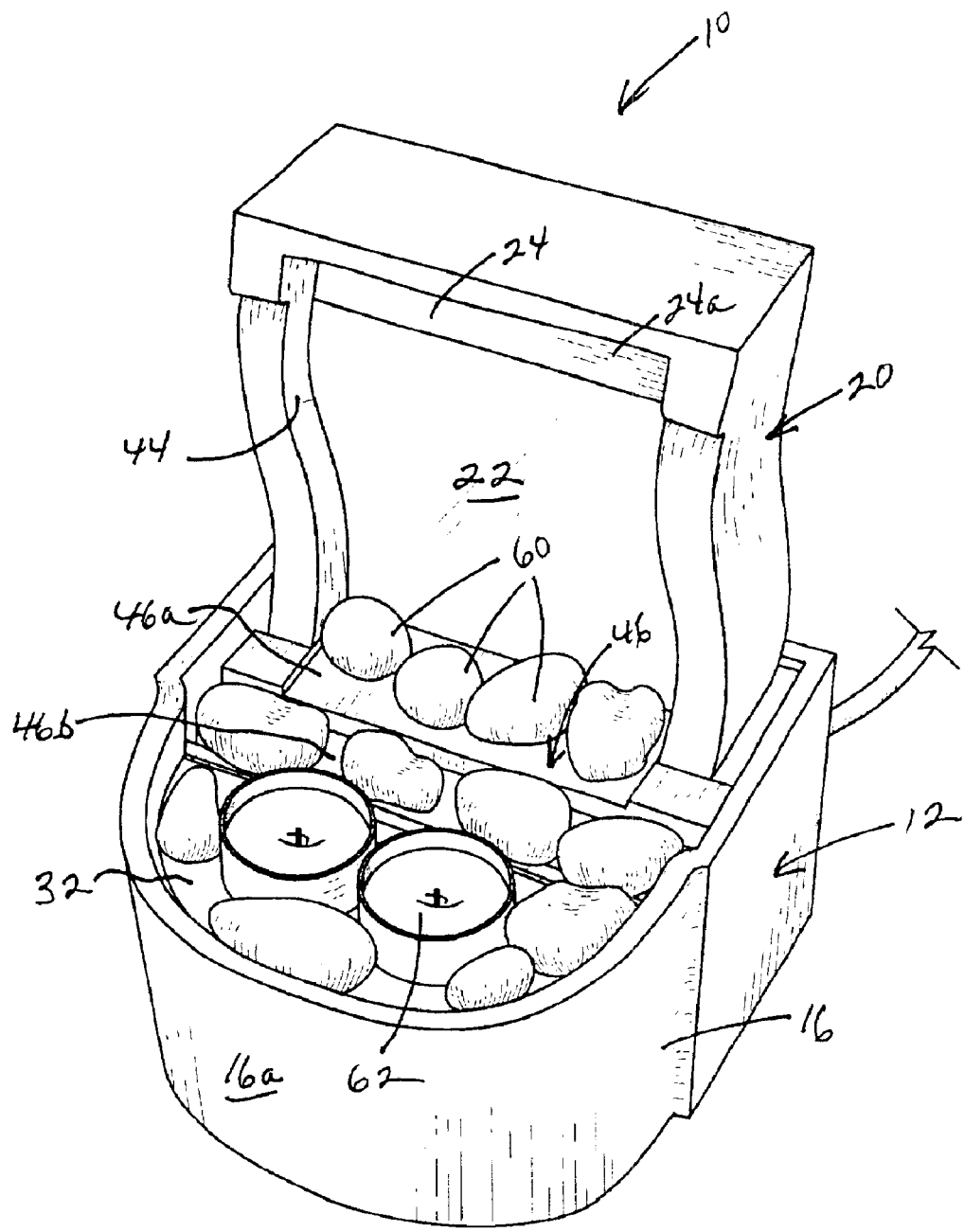
FIG. 1 is a perspective view of a portable relaxation and therapy device in accordance with the teachings of the disclosure.
Figure 2:
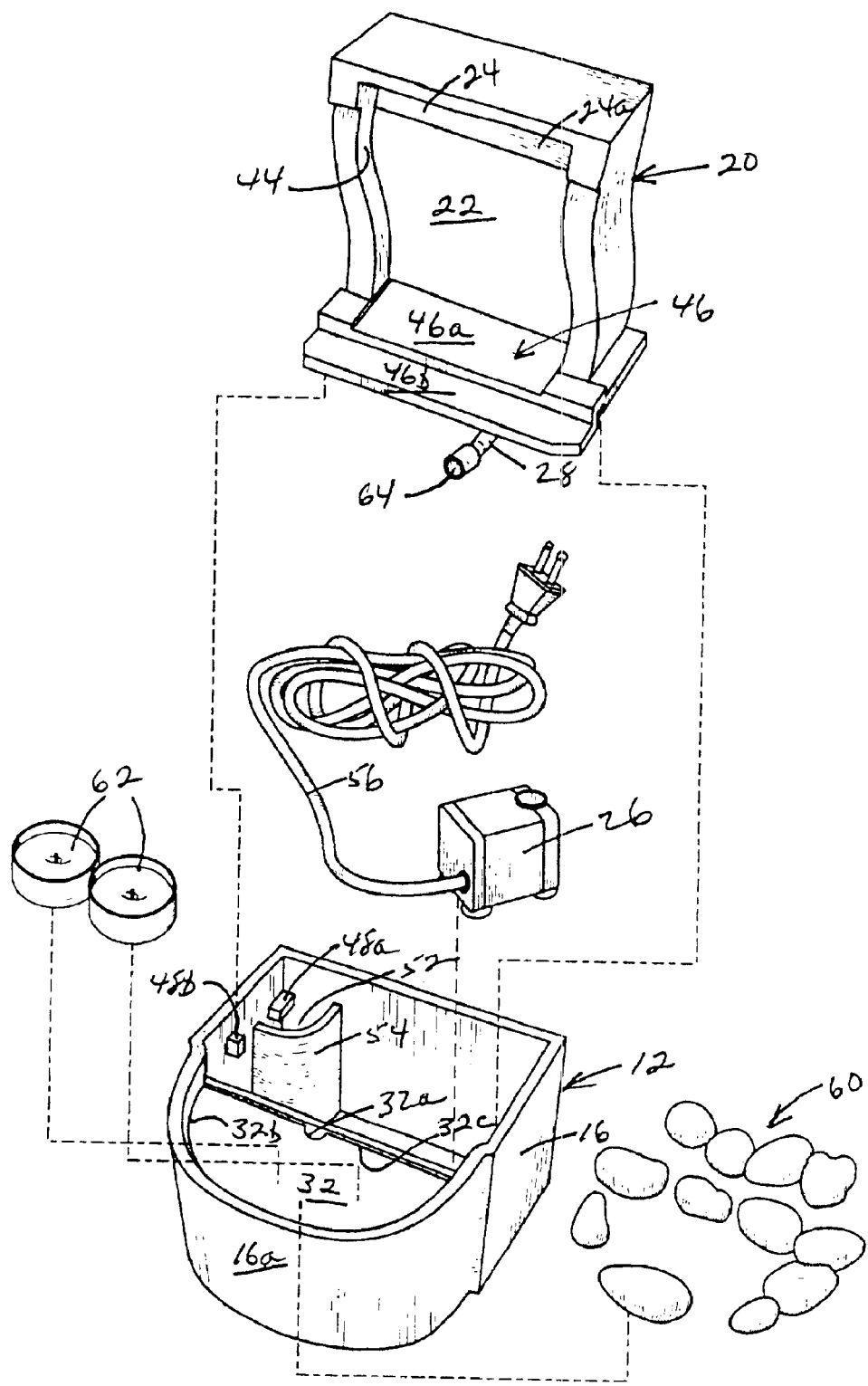
FIG. 2 is an exploded perspective view illustrating the portable device of FIG. 1 when provided it is provided in kit form.

Referring to FIGS. 1 and 2, the reference numeral 10 designates generally a portable relaxation and therapy device and kit constructed in accordance with the disclosure. The device 10 includes a liquid retention basin which is generally designated 12 having a bottom wall 14 (see FIG. 4) and a perimeter wall 16 upstanding from the bottom wall 14 to define at least one liquid chamber 18 therewithin. In addition, a waterfall wall 20 having a reflecting surface 22 is provided to extend generally upwardly from the retention basin 12 to a liquid dispersing waterfall ledge 24 thereabove (see, also, FIG. 3).

Figure 3:
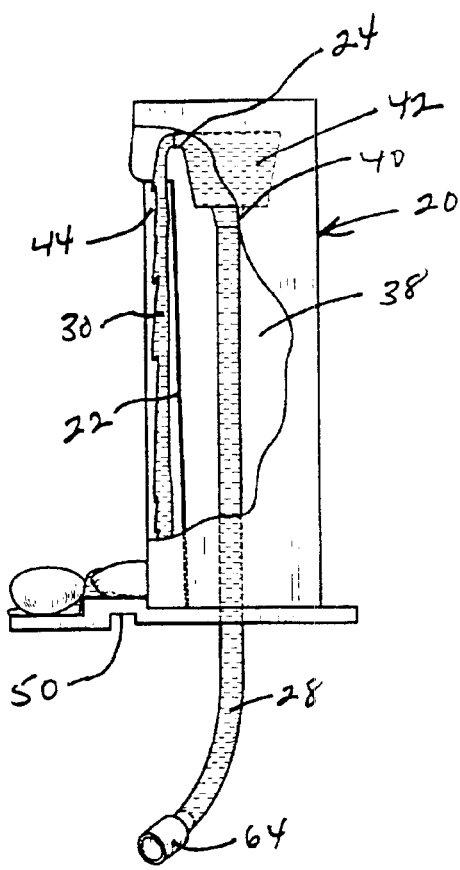
FIG. 3 is an end elevational view, partially broken away, of a waterfall wall for the portable device and kit of FIGS. 1 and 2.
Figure 4:
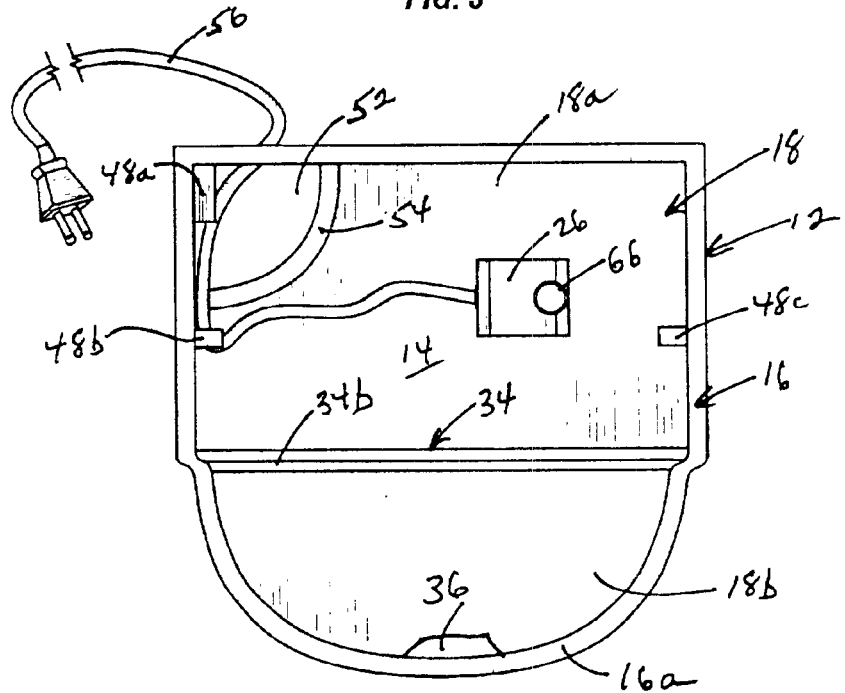
FIG. 4 is a top plan view of a liquid retention basin with the pump in place for the portable device and kit of FIGS. 1 and 2.

Referring specifically to FIGS. 3 and 4, the device 10 includes a pump 26 disposed in the liquid chamber 18 which is adapted to be in communication with a tube 28. The tube 28 directs a liquid such as water from the retention basin 18 upwardly to the waterfall ledge 24. With this arrangement, the waterfall ledge 24 causes water to cascade downwardly as at 30 to the liquid chamber 18 in front of the reflecting surface 22 of the waterfall wall 20.

Referring to FIGS. 1 and 2, the device 10 includes a cover 32 for the retention basin 12 disposed over at least a portion of the liquid chamber 18. The cover overlies and substantially isolates from view a liquid such as water in at least a forward portion of the retention basin 12, and also permits water cascading downwardly from the waterfall ledge 24 to return to the liquid chamber 18 as by means of a cutout as at 32a and/or a gap between the arcuate edge 32b of the cover 32 and the inner surface of the perimeter wall 16. In this manner, the water can be recirculated by the pump 26 from the liquid chamber 18 through the tube 28 to the waterfall ledge 24.

In the illustrated embodiment, the liquid retention basin 12 includes a partition wall 34 generally defining a pair of liquid chambers 18a and 18b which are in communication with one another through an opening 34a in the partition 34 adjacent the bottom wall 14. The partition wall 34 also has an upper edge 34b in the form of a step to define a cover-supporting lip, and the retention basin 12 includes a cover support 36 on an inner surface of the peripheral wall 16 generally opposite the cover-supporting lip 34b. The partition wall 34 of the retention basin 12 is generally planar and the peripheral wall 16 opposite the cover-supporting lip is generally arcuate as at 16a to define a generally semi-cylindrical opening to the liquid chamber 18b. With this arrangement, the generally semi-cylindrical opening leading to the liquid chamber 18b is in a forward portion of the retention basin 12, and the cover 32 is generally semi-cylindrical to fit loosely within the generally semi-cylindrical opening leading to the liquid chamber 18b, as previously described.

More specifically, and as previously described above, the generally semi-cylindrical cover 32 is suitably dimensioned so as to provide a gap between the inner surface of the peripheral wall as at 16a and the corresponding edge 32b of the cover 32. Also as previously described above, the generally semi-cylindrical cover 32 includes a generally semi-cylindrical cutout 32a positioned along an edge 32c of the cover 32 that rests on the cover-supporting lip 34b defined by the upper edge of the partition wall 34.

Referring now to FIG. 3, the waterfall wall 20 preferably includes a hollow chamber 38 behind the reflecting surface 22 and the tube 28 extends through the hollow chamber 38 to adjacent the waterfall ledge 24 as at 40. It will be seen that the tube 28 may feed into a liquid collection chamber 42 that will fill with water flowing from the liquid chamber 18 through the tube 28 by reason of the pump 26. When the liquid chamber 42 is full of water, additional water pumped through the tube 28 will spill over the waterfall ledge 24 to produce a cascading sheet of water as at 30 in front of the reflecting surface 22.

As shown in FIG. 3, the waterfall ledge 24 is disposed in overlapping relation to the reflecting surface 22, and the waterfall ledge 24 and reflecting surface 22 are both disposed in recessed relation within a frame defined by the waterfall wall 20 as at 44 (see, also, FIG. 1). It will also be seen from FIG. 3 that the reflecting surface 22 may be disposed at an inwardly and downwardly inclined angle to the vertical to more advantageously expose reflections in a manner to be described below. The waterfall wall 20 terminates in at least one splash plate generally designated 46 at the lower end thereof (see FIG. 2). The waterfall wall 20 is preferably configured to terminate in a pair of splash plates 46a and 46b at the lower end thereof disposed at the bottom of the reflecting surface 22 so as to lead generally in a step-like manner to the cover 32. The retention basin 12 may include a plurality of waterfall wall supports such as 48a, 48b, and 48c on an inner surface of the peripheral wall 16 for supporting the waterfall wall 20 so as to be in a generally vertical orientation (see FIGS. 2 and 4). The bottom surface of the waterfall wall 20 will then be provided with appropriate cutouts such as 50 which are adapted to receive the waterfall wall supports such as 48c in order to retain the waterfall wall 20 securely in position when it is supported by the retention basin 12. While not specifically shown, it will be appreciated that the bottom surface of the waterfall wall 20 will include similar cutouts appropriately sized and positioned to receive the waterfall wall supports 48a and 48b.

Figure 5:
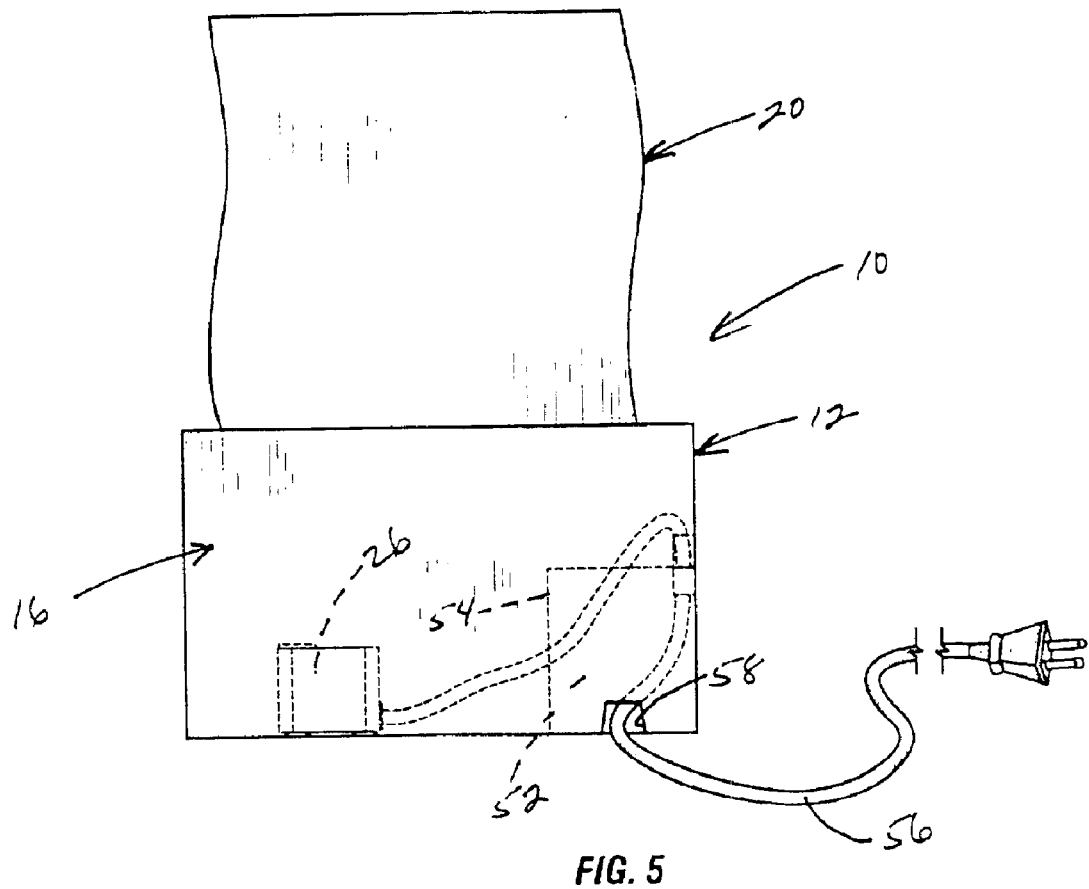
FIG. 5 is a rear elevational view of the portable device and kit of FIGS. 1 and 2 when the components have been assembled.
Figure 6:
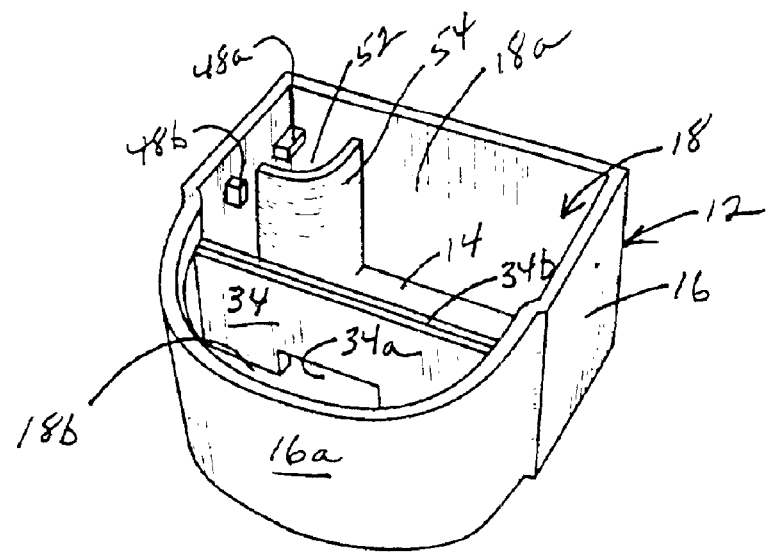
FIG. 6 is a perspective view of the liquid retention basin with the pump removed showing additional structural features.

Referring to FIGS. 4–6, the retention basin 12 includes a cord chamber 52 defined by an internal wall 54 integral with the bottom wall 14 and the peripheral wall 16 to extend a pump electrical cord 56 from the retention basin 12. The internal wall 54 shown is arcuate and the bottom wall 14 of the retention basin 12 does not extend into the region defining the cord chamber 52. As a result, the pump electrical cord 56 can extend downwardly through the cord chamber 52 and be disposed in a notch 58 in the rear of the perimeter wall 16 so the device 10 is able to sit completely flat on a horizontal surface.

While the portable relaxation and therapy device 10 can be manufactured as an entirely integral structure, it is contemplated by this disclosure to provide a portable relaxation and therapy kit as best appreciated from FIG. 2. The kit will basically include the components that have been described in significant detail above and, in addition, may include a plurality of polished stones or rocks generally designated 60 to be disposed on the cover 32 and the splash plates 46a and 46b and at least one aroma tea candle 62 to be placed at a lower end of the reflecting surface 22 of the waterfall wall 20, preferably on the cover 32 outwardly of the reflecting surface 22. With this arrangement, the various components that make up the portable relaxation and therapy kit 10 can be easily assembled to place the kit in a form to be operated in the form illustrated in FIG. 1.

More specifically, the pump 26 can be placed in the liquid chamber 118a following which the electrical cord 56 can be fed through the cord chamber 52 and positioned in the notch 58. Next, the waterfall wall 20 can be positioned adjacent the retention basin 12 so that the fitting 64 provided on the lower end of the tube 28 can be secured to a mating fitting 66 provided on the pump 26. Then the waterfall wall 20 can be placed in position on the retention basin 12 by placing the waterfall wall supports 48a, 48b, and 48c in the cutouts such as 50 in the bottom surface of the waterfall wall 20. Next, a liquid such as water can be placed in the liquid chamber 118b which will equalize in the chamber 18a by reason of the cutout 34a in the partition wall 34. Then, the cover 32 can be placed in position for support by the cover-supporting lip 34b on the partition wall 34 and the cover support 36. Next, the aroma tea candle or candles 62 can be placed on the cover 32, and the polished stones or rocks 60 can be placed about the splash plates 46a and 46b and the cover 32.

When these steps have been completed, the electrical cord 56 can be plugged into a suitable electrical outlet to operate the fully assembled portable relaxation and therapy kit.

From the foregoing, it will be appreciated that the device and kit of the disclosure accomplishes the objective of waterflow therapy by directing a cascading sheet of water in front of a reflecting surface such as a glass mirror. The reflecting surface or mirror 22 is set at a downwardly and inwardly disposed angle to cause reflections of fire from the flame of the aroma tea light 62 to show through the cascading sheet of water which produces a calming effect through both the direct and indirect views of the aroma tea light flames. By placing the reflecting surface or mirror 22 in a channel within the frame 44, a planar reflecting surface or mirror 22 can be used, and moisture penetration can be prevented by using a silicone seal in the channel of the frame 44.

In addition, it is contemplated that the frame 44 will be suitably formed to have a depth sufficient to prevent water from splashing off the downwardly and inwardly inclined and recessed reflecting surface or mirror 22. The two splash plates 46a and 46b at the bottom of the reflecting surface or mirror 22 allow the water to flow downwardly and eventually into the liquid chambers 18a and 18b to thereby prevent water overflow and allow maximum flame reflection when aroma tea lights are used. Still further, the cover 32 is removable to permit an alternative use upon removal by providing an open pond concept when not in position to support the polished stones or rocks 60 and the aroma tea lights 62. Still further, the generally arcuate peripheral wall 16a opposite the cover-supporting lip 34b may have a downward curve to maximize the visual effect. It makes it possible to clearly view water flowing down the splash plates 46a and 46b onto the cover 32 or, alternatively, into an open pond defined by the liquid chamber 18b. It is also advantageous for the waterfall ledge 24 to have ridges as at 24a to produce a water flowing sound for additional therapeutic effects. It is also the case that the ridges as at 24a assist the water in flowing evenly over the reflecting surface or mirror 22 to produce the cascading sheet of water. With the device and kit of the disclosure, the therapies produced by water, mirrors, candles, and aroma have been successfully combined into a single device or kit.

While in the foregoing there have been set forth preferred embodiments of the invention, it will be appreciated that the details herein given may be varied by those skilled in the art without departing from the true spirit and scope of the appended claims.

What is claimed is:

1. A portable relaxation and therapy device, comprising:
    a liquid retention basin having a bottom wall and a perimeter wall upstanding from the bottom wall to define at least one liquid chamber therewithin;
    a waterfall wall having a reflecting surface extending generally upwardly from the retention basin to a liquid dispersing waterfall ledge thereabove,
    the waterfall wall covering a rearward portion of the liquid chamber and causing a forward portion of the liquid chamber to define an open pond; and
    a pump disposed in the liquid chamber in communication with a tube for directing liquid in the retention basin upwardly to the waterfall ledge;
    the waterfall ledge overlapping the waterfall wall to cause liquid to cascade downwardly to the liquid chamber of the retention basin in front of the reflecting surface of the waterfall wall.

2. The device of claim 1 including a removable cover for the retention basin disposed over the forward portion of the liquid chamber to overlie the open pond and substantially isolate from view liquid in the retention basin.

3. The device of claim 2 wherein the removable cover includes a perimeter space for liquid cascading downwardly from the waterfall ledge in front of the reflecting surface of the waterfall wall to return to the liquid chamber.

4. The device of claim 1 wherein the liquid retention basin includes a partition wall generally defining a pair of liquid chambers in communication with one another through an opening in the partition wall adjacent the bottom wall.

5. The device of claim 4 wherein the partition wall has an upper edge defining a cover-supporting lip, the retention basin including a cover support on an inner surface of the peripheral wall opposite the cover-supporting lip.

6. The device of claim 5 wherein the partition wall of the retention basin is generally planar and the peripheral wall opposite the cover-supporting lip is generally arcuate to define a generally semi-cylindrical opening.

7. The device of claim 6 wherein the generally arcuate peripheral wall has a downward curve to maximize the visual effect of the open pond defined by the forward portion of the liquid chamber in the retention basin.

8. The device of claim 6 wherein the generally semi-cylindrical opening is in a forward portion of the retention basin and the cover is generally semi-cylindrical to fit loosely within the generally semi-cylindrical opening.

9. The device of claim 8 wherein the generally semi-cylindrical cover is dimensioned so as to provide a gap between the inner surface of the peripheral wall and a corresponding edge of the cover.

10. The device of claim 9 wherein the generally semi-cylindrical cover includes a cut-out positioned along an edge of the cover corresponding to the cover-supporting lip defined by the upper edge of the partition wall.

11. The device of claim 1 wherein the waterfall wall includes a hollow chamber behind the reflecting surface and the tube extends from the pump and through the hollow chamber to adjacent the waterfall ledge.

12. The device of claim 11 wherein the tube extends to a liquid collection chamber to be filled by the pump from liquid in the liquid chamber of the retention basin to spill over the waterfall ledge in a cascading sheet.

13. The device of claim 1 wherein the waterfall ledge is disposed in overlapping relation to the reflecting surface and the waterfall ledge and reflecting surface are both disposed in recessed relation within a frame.

14. The device of claim 13 wherein the waterfall ledge includes a plurality of generally horizontal ridges to produce a horizontally dispersed cascading sheet of liquid in front of the reflecting surface of the waterfall wall.

15. The device of claim 1 wherein the reflecting surface is disposed at an inwardly and downwardly inclined angle to the vertical and the waterfall wall terminates in at least one splash plate at the lower end thereof.

16. The device of claim 15 wherein the waterfall wall terminates in a pair of splash plates at the lower end thereof disposed at the bottom of the reflecting surface so as to lead generally in a step-like manner to the cover.

17. The device of claim 1 wherein the retention basin includes a plurality of waterfall wall supports on an inner surface of the peripheral wall for supporting the waterfall wall so as to be in a generally vertical orientation.

18. The device of claim 1 wherein the retention basin includes a cord chamber defined by an internal wall integral with the bottom wall and peripheral wall to extend an electrical cord of the pump from the retention basin.

19. A portable relaxation and therapy kit, comprising:

a liquid retention basin having a bottom wall and a perimeter wall upstanding from the bottom wall to define at least one liquid chamber therewithin;

a waterfall wall having a reflecting surface to be supported by the retention basin to extend generally upwardly to a liquid dispersing waterfall ledge thereabove;

a pump to be disposed in the liquid chamber and connected to a tube in the waterfall wall to direct liquid in the retention basin upwardly to the waterfall ledge;

the waterfall ledge causing liquid to cascade downwardly to the liquid chamber of the retention basin in front of the reflecting surface of the waterfall wall;

a cover for the retention basin to be disposed over the liquid chamber to overlie and substantially isolate liquid in at least a portion of the retention basin from view;

the cover permitting liquid cascading downwardly from the waterfall ledge in front of the reflecting surface of the waterfall wall to return to the liquid chamber; and a plurality of rocks and at least one aroma tea candle to be placed at a lower end of the reflecting surface of the waterfall wall.

20. The kit of claim 19 wherein the liquid retention basin includes a partition wall generally defining a pair of liquid chambers in communication with one another through an opening in the partition wall adjacent the bottom wall, the partition wall having an upper edge defining a cover-supporting lip and the retention basin including a cover support on an inner surface of the peripheral wall opposite the cover-supporting lip.

21. The kit of claim 20 wherein the partition wall of the retention basin is generally planar and the peripheral wall opposite the cover-supporting lip is generally arcuate to define a generally semi-cylindrical opening, the generally semi-cylindrical opening being in a forward portion of the retention basin and the cover being generally semi-cylindrical to fit loosely within the generally semi-cylindrical opening.

22. The kit of claim 21 wherein the generally semi-cylindrical cover is dimensioned so as to provide a gap between the inner surface of the peripheral wall and a corresponding edge of the cover, the generally semi-cylindrical cover including a cut-out positioned along an edge of the cover corresponding to cover-supporting lip defined by the upper edge of the partition wall.

23. The kit of claim 19 wherein the waterfall wall includes a hollow chamber behind the reflecting surface and the tube extends through the hollow chamber adjacent the waterfall ledge for attachment to the pump, the waterfall ledge being disposed in overlapping relation to the reflecting surface and the waterfall ledge and reflecting surface both being disposed in recessed relation within a frame.

24. The kit of claim 19 wherein the reflecting surface is disposed at an inwardly and downwardly inclined angle to the vertical when supported by the retention basin to extend generally upwardly, and the waterfall wall terminates in a pair of splash plates at the lower end thereof disposed at the bottom of the reflecting surface so as to lead generally in a step-like manner to the cover when supported by the retention basin.

25. The kit of claim 19 wherein the retention basin includes a plurality of waterfall wall supports on an inner surface of the peripheral wall for supporting the waterfall wall so as to be in a generally vertical orientation, the retention basin also including a cord chamber defined by an internal wall integral with the bottom wall and peripheral wall to extend an electrical cord of the pump outwardly of the retention basin.

\* \* \* \* \*